(12) United States Patent
Ledwith

(10) Patent No.: US 8,499,763 B2
(45) Date of Patent: Aug. 6, 2013

(54) CONNECTOR FOR COUPLING A TRACHEAL TUBE TO AN AUXILIARY DEVICE

(75) Inventor: Brian Ledwith, Ballymahon (IE)

(73) Assignee: Covidien LP, Mansfield, MA (US)

( * ) Notice: Subject to any disclaimer, the term of this patent is extended or adjusted under 35 U.S.C. 154(b) by 1023 days.

(21) Appl. No.: 12/533,188

(22) Filed: Jul. 31, 2009

(65) Prior Publication Data

US 2011/0023875 A1 Feb. 3, 2011

(51) Int. Cl.
*A61M 15/08* (2006.01)
(52) U.S. Cl.
USPC ............ 128/207.18; 128/200.24; 128/207.15
(58) Field of Classification Search
USPC ............ 128/200.24, 200.26, 207.14–207.18
See application file for complete search history.

(56) References Cited

U.S. PATENT DOCUMENTS

| | | |
|---|---|---|
| 2,002,121 A | 5/1935 | McMaster |
| 4,146,034 A | 3/1979 | Gupta |
| 4,152,017 A | 5/1979 | Abramson |
| 4,369,991 A | 1/1983 | Linder |
| 4,475,548 A | 10/1984 | Muto |
| 4,584,998 A | 4/1986 | McGrail |
| 4,593,690 A | 6/1986 | Sheridan et al. |
| 4,683,879 A | 8/1987 | Williams |
| 4,840,173 A | 6/1989 | Porter, III |
| 4,909,248 A | 3/1990 | McLennan Anderson |
| 5,033,466 A | 7/1991 | Weymuller, Jr. |
| 5,174,283 A * | 12/1992 | Parker ................. 128/200.26 |
| 5,251,617 A | 10/1993 | Linder |
| 5,287,852 A * | 2/1994 | Arkinstall ............ 128/207.14 |
| 5,339,805 A * | 8/1994 | Parker ................. 128/200.26 |
| 5,582,166 A | 12/1996 | Lee |
| 5,591,130 A | 1/1997 | Denton |
| 5,794,986 A | 8/1998 | Gansel et al. |
| 5,864,938 A | 2/1999 | Gansel et al. |
| 5,885,248 A | 3/1999 | Denton |
| 5,906,204 A | 5/1999 | Beran et al. |
| 6,155,252 A * | 12/2000 | Warters ............... 128/200.24 |
| 6,849,042 B2 | 2/2005 | Christopher |
| 7,261,105 B2 | 8/2007 | Fukunaga et al. |
| 7,418,965 B2 | 9/2008 | Fukunaga et al. |
| 7,503,328 B2 | 3/2009 | Kolobow et al. |
| 2008/0142003 A1* | 6/2008 | Depel ................. 128/200.24 |
| 2009/0229605 A1* | 9/2009 | Efrati et al. ............ 128/203.12 |

FOREIGN PATENT DOCUMENTS

| | | |
|---|---|---|
| CA | 2 463 538 A1 | 4/2003 |
| DE | 2045870 B1 | 2/1972 |
| DE | 2211173 A1 | 9/1973 |
| DE | 8800380 U1 | 2/1988 |
| DE | 19960046 C1 | 5/2001 |

(Continued)

OTHER PUBLICATIONS

International Search Report PCT/US2010/041309, 4 pages, mailed Sep. 24, 2010.

(Continued)

*Primary Examiner* — Glenn Richman

(57) ABSTRACT

Various embodiments of a connector assembly are provided to removably couple a proximal end of a tracheal tube to components associated with a ventilator or an anesthesiology machine. The disclosed embodiments include a compression fitting, which creates an airtight seal between walls of the tracheal tube and components of the compression fitting, thus allowing air to flow to and from a patient.

14 Claims, 5 Drawing Sheets

FOREIGN PATENT DOCUMENTS

| | | |
|---|---|---|
| EP | 0064315 A2 | 11/1982 |
| EP | 1521026 A2 | 4/2005 |
| EP | 1783414 A1 | 5/2007 |
| GB | 1421452 A | 1/1976 |
| GB | 2028139 A | 3/1980 |
| WO | 9824500 A1 | 6/1998 |

OTHER PUBLICATIONS

Cook Medical, "Arndt Endobronchial Blocker", http://www.cookmedical.com/cc/dataSheet.do?id=3988, Mar. 2010, pp. 1-2.

Cook Medical, "Cohen Endobronchial Blocker", http://www.cookmedical.com/cc/dataSheet.do?id=3989, Mar. 2010, pp. 1-2.

Hudson RCI—Teleflex Medical, "FLEX-C-PAP", Apr. 2010, pp. 1-4 (pp. 3-4).

Sheidan LITA Cuffed Endotracheal Tube—Teleflex Medical—Hudson RCI, Apr. 2010, pp. 1-4 (pp. 3-4).

Sheridan Preformed Oral Endotracheal Tubes—Teleflex Medical—Hudson RCI, Apr. 2010, pp. 1-3.

Sheidan STAT-MED Cuffed Endotracheal Tube—Teleflex Medical—Hudson RCI, Apr. 2010, pp. 1-4 (pp. 1-2).

\* cited by examiner

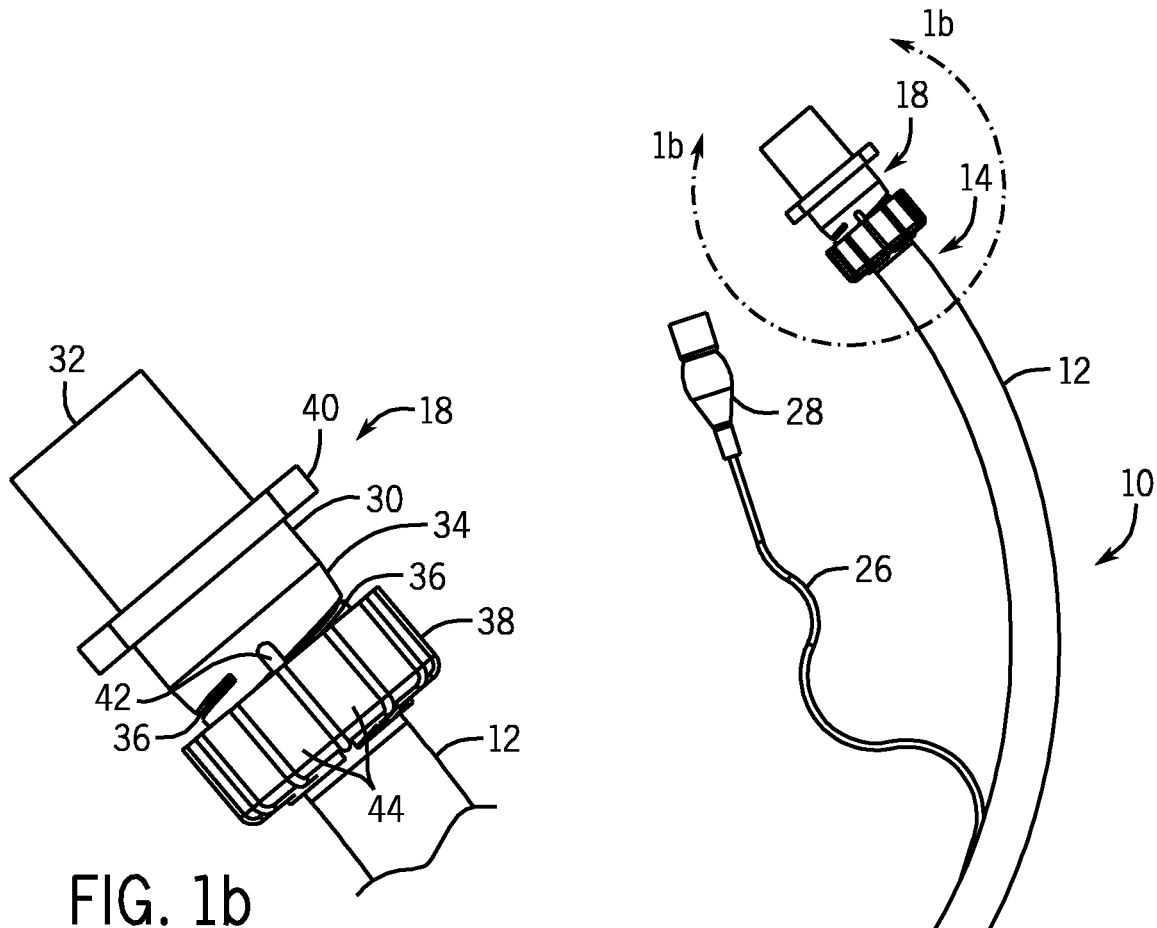
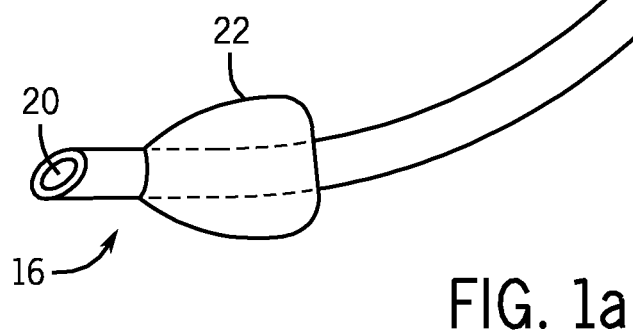
FIG. 1b
FIG. 1a

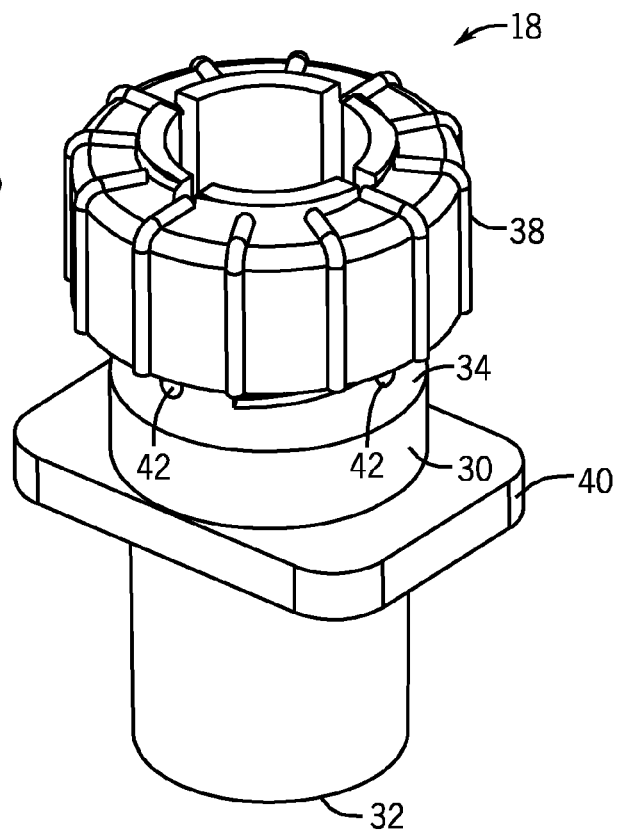
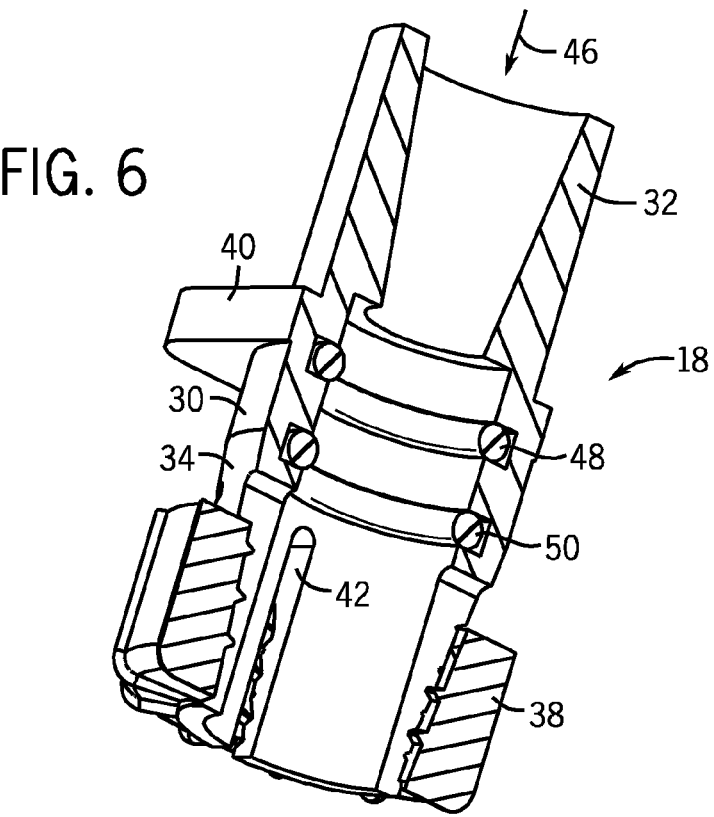

CONNECTOR FOR COUPLING A TRACHEAL TUBE TO AN AUXILIARY DEVICE

BACKGROUND

The present disclosure relates generally to medical devices and, more particularly, to airway devices, such as tracheal tubes.

This section is intended to introduce the reader to aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Conventional tracheal tubes are supplied in standard lengths and sizes and are chosen for a patient mainly based on their size and age. Such tracheal tubes are typically used in conjunction with connectors, which facilitate coupling of the proximal end of the tracheal tube to tubing associated with a ventilator or an anesthesiology machine. These connectors typically include a cylindrical section of the standard fifteen millimeter size for mating with conventional tracheal tubes. Due to variability in patient size and differences in the sizes and lengths of conventional tracheal tubes, anesthesiologists often find it necessary to shorten the length of the proximal (external) end of the tracheal tube such that the end of the tracheal tube is closer to the intubation site. To this end, anesthesiologists often remove a portion of the tracheal tube by cutting, thus allowing the tracheal tube, any associated connectors and any auxiliary tubing to be easily attached to the patient, eliminating inadvertent movement during use.

Tracheal tubes are often placed in the airway of a patient in emergency medical situations, such as when a patient experiences cardiac or respiratory arrest, which necessitate protection of the airway from possible obstruction or occlusion in a timely manner. Oftentimes, tracheal tubes are supplied by the manufacturer with the connector already attached to the proximal end of the tracheal tube. Because shortening of such tubes requires the anesthesiologist to remove the connector from the proximal end of the tracheal tube, cut the tracheal tube, and reinsert the connector in the tracheal tube, valuable time is consumed in emergency situations. Additional time is often consumed because it can be difficult to reinsert conventional connectors back into the cut end of the tracheal tube. For instance, the traditional connector and tracheal tube T shown in FIG. 7 illustrate the drawbacks of conventional connectors. The extension E of the connector that must be reinserted into the tracheal tube T after cutting has an outer diameter d. To fit this end of the connector into the tracheal tube T, a flaring device must be used to expand the tracheal tube T from a normal opening size N to a flared opening size F. This flaring expands the inner diameter of the tube T to diameter D, such that the extension E of the connector may be reinserted into the tube T. Upon reinsertion of the traditional connector, the force required to pull the connector from the tube may be greatly reduced, thus increasing the risk of undesirable dislodging of the connector from the tracheal tube during use. This inadvertent dislodging can disconnect the ventilator, thus breaking the breathing circuit, which presents high risk to the patient. Accordingly, there exists a need for improved connectors that provide secure and efficient attachment and reattachment for tracheal tubes.

BRIEF DESCRIPTION OF THE DRAWINGS

Advantages of the present disclosure may become apparent upon reading the following detailed description and upon reference to the drawings in which:

FIG. 1a illustrates an exemplary endotracheal tube removably attached to a connector assembly in accordance with aspects of the present disclosure;

FIG. 1b illustrates the proximal end of the endotracheal tube illustrated in FIG. 1a in accordance with aspects of the present disclosure;

FIG. 2 illustrates a cross sectional view of the proximal end of the endotracheal tube illustrated in FIG. 1a;

FIG. 5 is a perspective view of the exemplary connector assembly;

FIG. 6 is a sectional view of the exemplary connector assembly of FIG. 5; and

DETAILED DESCRIPTION OF SPECIFIC EMBODIMENTS

Figure 2:
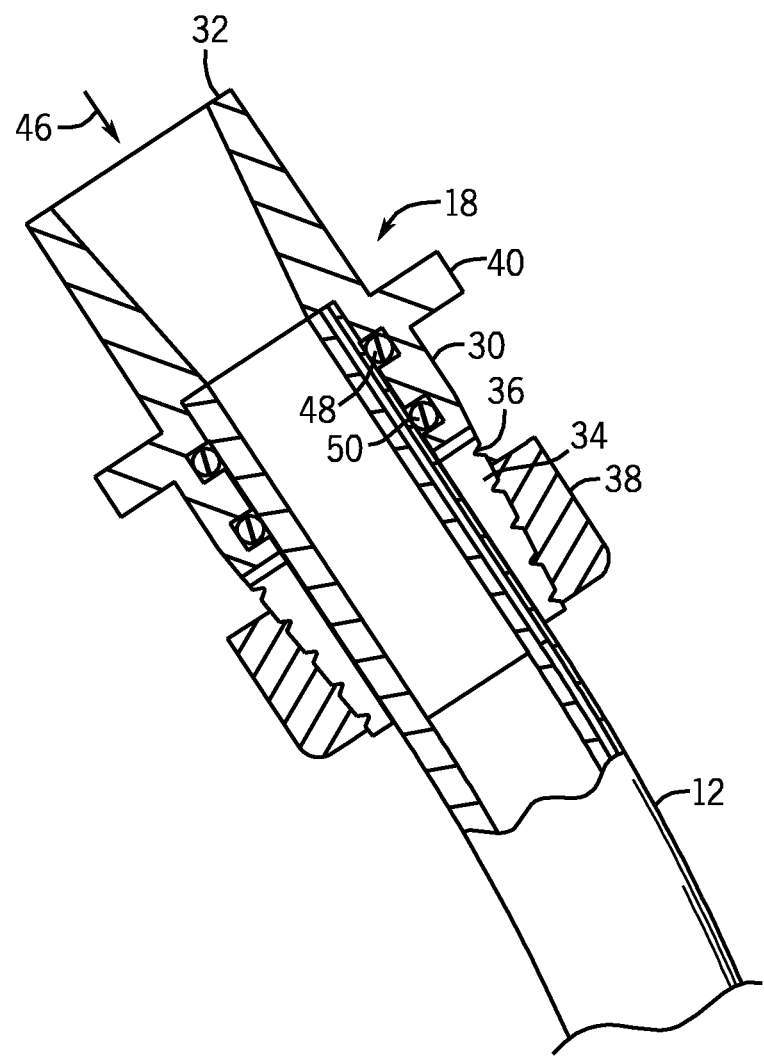

One or more specific embodiments of the present disclosure will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As discussed in further detail below, various embodiments of a connector assembly are provided to removably couple a proximal end of a tracheal tube to components associated with a ventilator or an anesthesiology machine. The connector assembly is removable rather than permanent, capable of being attached to a cut tracheal tube, capable of attaching to a tracheal tube without the use of a flaring device, capable of allowing a smooth transition between the connector and the tracheal tube, and so forth. The disclosed embodiments include a compression fitting, which creates an airtight seal between walls of the tracheal tube and components of the compression fitting, thus allowing air to flow to and from a patient. In one embodiment, the connector assembly includes two o-lings, which are configured to lodge in the compression fitting and create the airtight seal. The foregoing features, among others, may have the effect of increasing both the pull force necessary to remove the connector assembly from the tracheal tube and the ease and efficiency of tracheal tube shortening.

Disclosed embodiments may offer distinct advantages over traditional connectors since use of the connector assembly does not require an original connector to be reinserted into the tracheal tube after shortening. Alternatively, present embodiments provide for the proximal end of the cut tracheal tube to be placed inside the connector assembly with ease. This feature may have the effect of reducing the amount of time an anesthesiologist would otherwise spend flaring and reinserting the original connector in emergency situations in which time is a critical factor. Also, since the tracheal tube fits inside the connector assembly, the inner diameter of the tracheal tube is maintained after tube shortening. That is, the inner diameter of the ventilator circuit does not change after reinsertion of the tracheal tube to the connector assembly, thus providing an unobstructed air pathway from the ventilator.

Additionally, present embodiments provide a secure attachment between the tracheal tube and the connector assembly via the use of a threaded nut, which provides a compressive force that prohibits the tracheal tube from dislodging from the connector assembly. In some embodiments, the secure attachment may allow for the connector assembly to be the sole means of connecting the tracheal tube to other components in the ventilator circuit. For instance, the connector assembly may be supplied with or on the tracheal tube for initial use. In such embodiments, the connector assembly may be used with a cut or uncut tracheal tube as desired.

Turning now to the drawings, FIG. 1a illustrates an exemplary endotracheal tube 10 in accordance with aspects of the present disclosure. The endotracheal tube 10 includes a central tubular body 12 with proximal and distal ends 14 and 16, respectively. In the illustrated embodiment, the proximal end 14 is outfitted with a connector assembly 18 that may be attached to a mechanical ventilator during operation. The distal end 16 terminates in an opening 20 and may be placed in a patient's trachea during operation to maintain airflow to and from the patient's lungs. As illustrated, a cuff 22 may be attached to the distal end 16 of the tubular body 12 that may be inflated to seal against the walls of a body cavity (e.g., the trachea). The cuff 22 may be inflated via an inflation lumen 26 connected to a fixture 28 located outside the patient during operation.

The tubular body 12 and the cuff 22 may be formed from materials having desirable mechanical properties (e.g., puncture resistance, pin hole resistance, tensile strength, and so forth) and desirable chemical properties (e.g., biocompatibility). In one embodiment, the walls of the cuff 22 may be made of a polyurethane (e.g., Dow Pellethane® 2363-80A) having suitable mechanical and chemical properties. In other embodiments, the walls of the cuff 22 may be made of a suitable polyvinyl chloride (PVC). In certain embodiments, the cuff 22 may be generally sized and shaped as a high volume, low pressure cuff that may be designed to be inflated to pressures between about 15 cm $H_2O$ and 30 cm $H_2O$. In the illustrated embodiment the cuff 22 secures the endotracheal tube 10 in the body cavity of the patient. However, it should be noted that in alternative embodiments cuffless endotracheal tubes may be used in conjunction with present embodiments of the connector assembly 18.

FIG. 1b illustrates the connector assembly 18 in more detail. The connector assembly 18 includes a body 30 with a first end 32 that is configured to attach to components of a ventilator or anesthesiology machine, such as tubing, connectors, and so forth. The body 30 also includes a second end 34 with threads 36 that are configured to engage a locking nut 38. An extension 40 of the body 30 may be used by a physician to grip and place the second end 34 of the body 30 around the endotracheal tube 10 during operation. The second end 34 of the body 30 also includes one or more slits 42 that facilitate the compression of the second end 34 when the locking nut 38 is threadably engaged with the body 30 during use. The locking nut 38 includes ridges 44, which allow the user to thread the locking nut 38 on the body 30. It should be noted that other types of compression may be used in further embodiments to secure a connector to the tracheal tube. For instance, in one embodiment, a ferrule fitting may be used in place of the connector assembly 18 illustrated in FIG. 1b. In such an embodiment, a ferrule ring may be placed around the tracheal tube, and a nut may be tightened around the ferrule ring such that it is tightened around the tracheal tube, thereby creating an airtight seal and holding the connector securely in place.

FIG. 2 is a cross sectional view of the connector assembly 18 attached to the tubular body 12 of the endotracheal tube 10. As illustrated, an aperture 46 in the first end 32 of the body 30 opens into a channel that extends axially throughout the connector assembly 18 and the tubular body 12 of the endotracheal tube 10. The inside of the first end 32 of the body 30 includes a wide portion at the aperture 46 that becomes narrower in diameter as it extends further into the body 30. At the narrowest end of the axial channel, an airtight seal is formed between the tubular body 12 of the endotracheal tube 10 and the body 30 of the connector assembly 18 via a first o-ring 48 and a second o-ring 50. That is, when the locking nut 38 is threadably engaged with the body 30 of the connector assembly 18, the o-rings 48, 50 function to ensure that airflow to and from the patient does not leak when in transit between the patient and the ventilator or anesthesiology machine. The seals also help to maintain the connector 18 on the outer surface of the endotracheal tube 10. In some embodiments, as in that illustrated, the tubular body 12 may be axially slid into the body 30 until it reaches an abutment, which may indicate proper positioning of the tubular body 12 in the body 30 of the connector assembly 18 to a user. It should be recognized that, while the illustrated embodiment utilizes two o-ring seals 48 and 50, other sealing arrangements may be employed in certain designs. Moreover, it may be possible to form the body of the connector 18 so as to perform the sealing function without the addition of separate sealing elements. For instance, the body of the connector 18 may be made of an elastomeric material or may be manufactured with an adhesive coating such that the body is self sealing.

As previously mentioned, the connector assembly 18 may be used in conjunction with conventional endotracheal tubes 10 in instances when an anesthesiologist finds it desirable to shorten the length of the proximal end 14 of the endotracheal tube 10 such that the external end of the endotracheal tube 10 is closer to the intubation site. Such instances may occur due to variability in patient size and differences in the sizes and lengths of conventional endotracheal tubes 10. In these instances, anesthesiologists may remove a portion of the endotracheal tube 10 by cutting, thus allowing the endotracheal tube 10, any associated connectors, and any auxiliary tubing to be easily attached to the patient via adhesives or straps, eliminating inadvertent movement during use. Shortening of such endotracheal tubes 10 traditionally requires the anesthesiologist to remove an originally supplied connector from the proximal end 14 of the endotracheal tube 10, to cut the endotracheal tube 10, and to reinsert the original supplied connector in the endotracheal tube 10. Reinsertion of the original connector may be difficult since the endotracheal tube 10 tends to constrict after cutting. Additionally, reinserted original connectors may have reduced pull-out force performance as compared to the original configuration.

Figure 3:
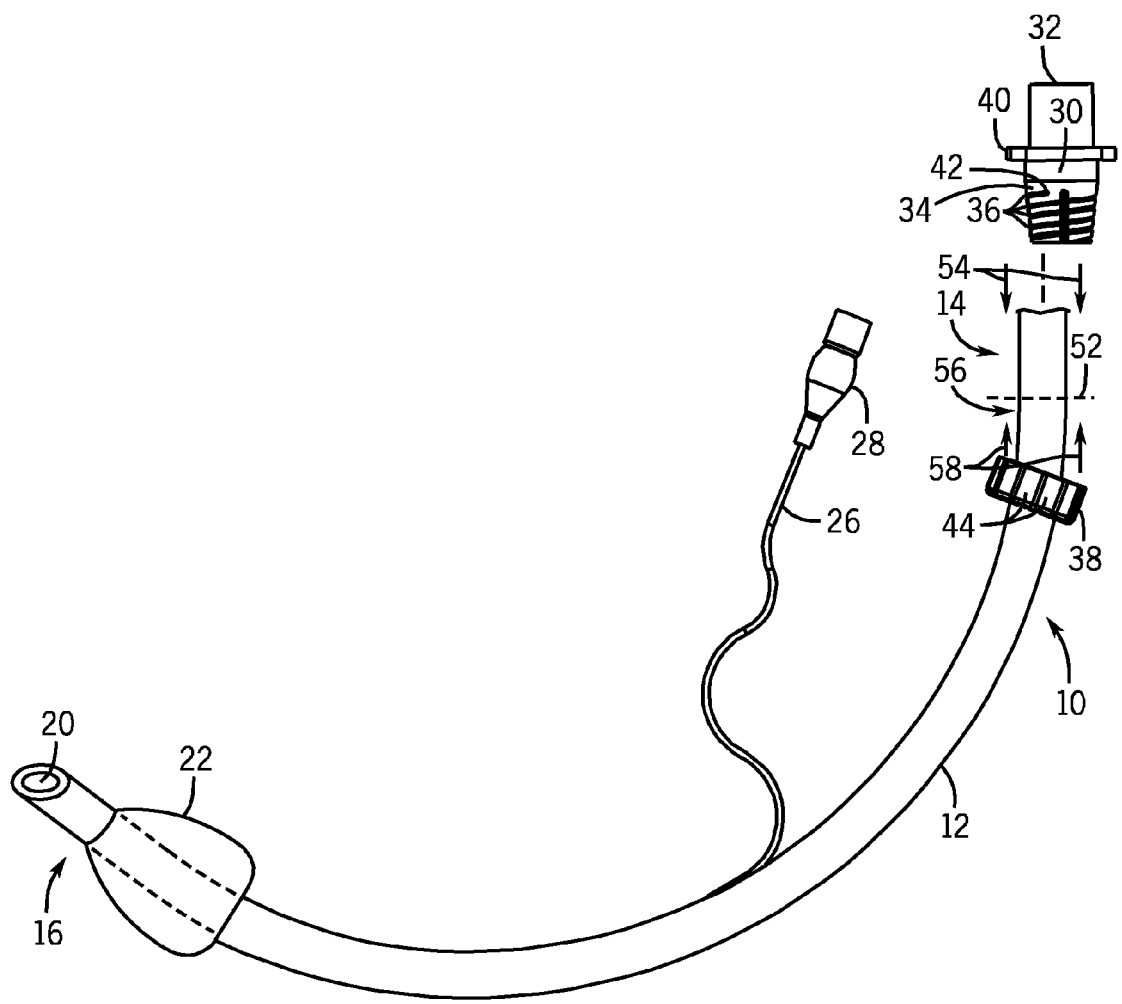
FIG. 3 illustrates an exemplary cut endotracheal tube prior to insertion of the threaded body of the connector in the proximal end of the endotracheal tube.

FIG. 3 illustrates how the exemplary connector assembly 18 may be used in conjunction with traditional endotracheal tubes 10 to alleviate some of the difficulties associated with conventional systems. In the illustrated embodiment, the proximal end 14 of the endotracheal tube 10 may be cut along dashed line 52 to shorten the tubular body 12. The locking nut 38 may then be axially slid onto the end of the tubular body 12 in the direction generally indicated by arrows 54, toward the distal end 16 of the tubular body 12. The second end 34 of the body 30 of the connector assembly 18 can then be axially slid in the direction of arrows 54 over a new proximal end 56 of the tubular body 12 such that the endotracheal tube 10 is received in the second end 34 of the body 30 of the connector assembly 18. Accordingly, in a presently contemplated embodiment, the diameter of the body 30, and the second end 34 that is configured to slide over the tubular body 12. The first end 32 is approximately fifteen millimeters, which is a standard size used for endotracheal tube connectors, although in certain embodiments, the connector may be sized to appropriately fit other ventilator circuits (e.g., 8 mm, 22 mm). Moreover, it should be noted that in alternative embodiments, the diameter of the second end 34 may be any dimension suitable for receiving tracheal tubes of various sizes.

Once the body 30 of the connector assembly 18 has been axially slid onto the new proximal end 56 of the tubular body 12, the locking nut 38 may be axially slid in the general direction of arrows 58 towards the new proximal end 56 and away from the distal end 16 of the tubular body 12. The locking nut 38 may then be threadably engaged with the threads 36 on the second end 34 of the body 30 of the connector assembly 18 via the ridges 44 that the user may grip and use to turn the locking nut 38. In some embodiments, owing to the taper of the threaded region of the body 30, advancement of the locking nut 38 onto the threads 36 tends to constrain and tighten the threaded region onto the outer surface of the tube 12 by exerting a radial force on the tube 12. It should be noted that in other embodiments, the threaded region of the body 30 may not be tapered. For instance, the threads may extend from a shallow region to a deeper region to keep the tracheal tube lodged in the connector 18. Applying a conventional pull force (i.e., an axial force in the general direction of arrows 58) once the connector assembly 18 has been locked on the tubular body 12 will not dislodge the endotracheal tube 10 from the connector assembly 18. Additionally, o-rings 48, 50 provide an airtight seal such that airflow through the tubular body 12 and the connector assembly 18 remains contained in the confines of the axial channel.

Figure 4:
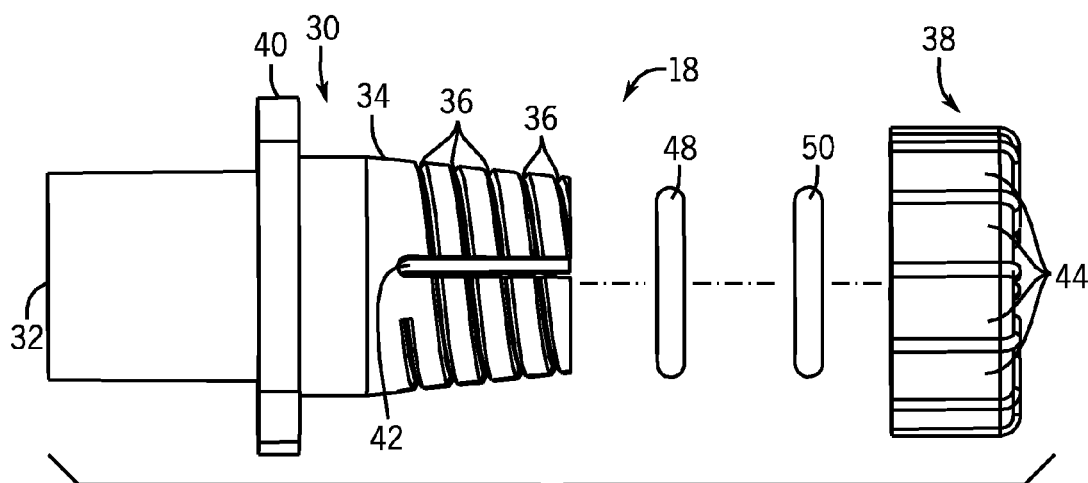
FIG. 4 is an exploded view of an exemplary connector assembly in accordance with aspects of the present disclosure.
Figure 7:
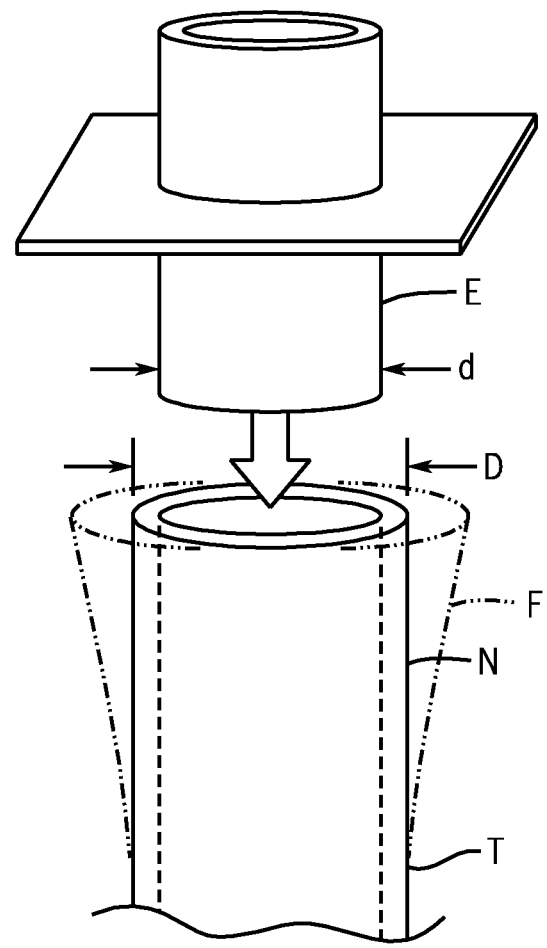
FIG. 7 is a perspective view of a conventional connector assembly as seen in the prior art.

FIGS. 4-6 are an exploded view, a perspective view, and a sectional view, respectively, of the connector assembly 18. FIG. 4 illustrates the body 30, the first o-ring 48, the second o-ring 50, and the locking nut 38 in more detail. As illustrated, the second end 34 of the body 30 extends from a portion of the body 30 with a larger diameter to a portion of the body 30 with a smaller diameter. This feature allows the body 30 to securely fit over and receive the tubular body 12 during use. In some embodiments, the body 30 may be made of Polyvinyl Chloride (PVC) or another suitable material. The first o-ring 48 and the second o-ring 50 are configured to lodge in the body 30 of the connector assembly 18 as shown in FIG. 6 and may be made of materials such as Nitrile or Viton or another suitable material. The locking nut 38 that engages with the threads on the body 30 and may be made of Polyvinyl Chloride (PVC) or another suitable material. In the presently contemplated embodiment shown, the body 30, as illustrated in FIG. 5, includes four slits 42. However, it should be noted that in other embodiments, the body 30 may contain more or fewer slits 42 as desired.

In certain embodiments, components of the connector assembly 18 may be replaceable, disposable, and/or able to be sterilized. For instance, the o-rings 48, 50 may be made of a suitable material such that they may be discarded and replaced as desired. Similarly, the entire connector assembly 18 may be made of suitable materials such that the assembly 18 may be removed from the endotracheal tube 10, sterilized via heat treatment or other suitable methods, and recoupled to the endotracheal tube 10. Alternatively, the connector assembly 18 may be made of suitable materials such that it may be discarded and replaced as desired for patients requiring long term care.

As noted above, various alternative configurations may be envisioned for the compression fitting and connector. In addition to those outlined above, the structure utilizing a body fitting over the tube end and a mating nut disposed around the tube may be reversed, or a multi-part connector may be employed with more than one body part, while still providing compressive securement to the tube end.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. An intubation system comprising:
   a tracheal tube configured to be placed in the trachea of a patient; and
   a connector assembly configured to be attached to the tracheal tube and to an auxiliary device comprising:
   a threaded body comprising a first end configured to receive an interface element of the auxiliary device and a second end comprising threads, the second end being configured to fit over a proximal end of the tracheal tube; and
   a locking nut comprising threads and a central opening configured to receive the tracheal tube there through, the locking nut being configured to be threaded onto the threaded body to lock the threaded body onto the proximal end of the tracheal tube.

2. The intubation system of claim 1, wherein the locking nut is configured to compressively retain a wall of the tracheal tube between the locking nut and the second end of the threaded body.

3. The intubation system of claim 1, comprising at least one sealing element disposed in the threaded body and configured to contact and seal against the tracheal tube.

4. The intubation system of claim 3, wherein the at least one sealing element is configured to create an airtight seal between the connector assembly and the tracheal tube.

5. The intubation system of claim 1, wherein the threaded body comprises at least one slit configured to permit radial contraction of the threaded body on the tracheal tube as the locking nut is threaded onto the threaded body.

6. The intubation system of claim 1, wherein the auxiliary device comprises a ventilator or an anesthesiology machine.

7. The intubation system of claim 1, wherein the threaded body and the locking nut are made of Polyvinyl Chloride (PVC).

8. The intubation system of claim 3, wherein the at least one sealing element is made of Nitrile or Viton.

9. An intubation system comprising:
   a tracheal tube; and
   a connector assembly coupled to the tracheal tube and configured to be coupled to an auxiliary device, wherein the connector assembly comprises:
   a locking portion comprising a first mating feature, wherein the locking portion is configured to slide axially along the exterior surface when the first mating feature is uncoupled; and
   a connector body comprising a first end configured to receive an interface element of the auxiliary device and a second end comprising a second mating feature configured to couple to the first mating feature of the locking portion, wherein the connector body and the locking portion, when coupled, are disposed about only the exterior of the tracheal tube.

10. The system of claim 9, wherein the connector assembly is configured to create an airtight seal between the connector assembly and the tracheal tube.

11. The system of claim 10, wherein the connector assembly comprises one or more sealing rings that are compressed between the connector body and the locking portion to create the airtight seal.

12. The system of claim 9, wherein the connector body comprises at least one slit configured to permit radial contraction of the threaded body on the tracheal tube when the locking portion is coupled to the connector body.

13. The system of claim 9, wherein the connector body comprises an expanded diameter when uncoupled to the locking portion and a compressed diameter when coupled to the locking portion.

14. The system of claim 9, wherein the connector body comprises a portion that tapers from a proximal end towards a distal end.

* * * * *